US006942996B2

(12) United States Patent
Bathe et al.

(10) Patent No.: US 6,942,996 B2
(45) Date of Patent: Sep. 13, 2005

(54) **ISOLATED POLYNUCLEOTIDE FROM *CORYNEBACTERIUM* ENCODING A HOMOCYSTEINE METHYLTRANSFERASE**

(75) Inventors: Brigitte Bathe, Salzkotten (DE); Bettina Moeckel, Duesseldorf (DE); Walter Pfefferle, Halle (DE); Klaus Huthmacher, Gelnhausen (DE); Christian Rueckert, Guetersloh (DE); Joern Kalinowski, Bielefeld (DE); Alfred Puehler, Bielefeld (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 226 days.

(21) Appl. No.: 09/919,835

(22) Filed: Aug. 2, 2001

(65) Prior Publication Data

US 2002/0110877 A1 Aug. 15, 2002

Related U.S. Application Data

(60) Provisional application No. 60/294,250, filed on May 31, 2001.

(30) Foreign Application Priority Data

Aug. 2, 2000 (DE) .......................................... 100 38 023
Feb. 28, 2001 (DE) .......................................... 101 09 689

(51) Int. Cl.$^7$ ............................ C12P 13/12; C12N 9/10; C12N 1/20; C12N 15/00; C07H 21/04
(52) U.S. Cl. ....................... 435/113; 435/69.1; 435/106; 435/183; 435/193; 435/252.3; 435/252.32; 435/252.8; 435/320.1; 536/23.2; 536/23.7
(58) Field of Search ................................ 435/69.1, 106, 435/113, 183, 193, 252.3, 252.32, 320.1; 536/23.2

(56) References Cited

FOREIGN PATENT DOCUMENTS

| DE | 196 44 567 | 4/1998 |
|---|---|---|
| EP | 0 387 527 | 9/1990 |
| WO | WO 98/18937 | 5/1998 |
| WO | WO 01/00802 | 1/2001 |
| WO | WO 01/00845 | 1/2001 |
| WO | WO 01/00847 | 1/2001 |

OTHER PUBLICATIONS

U.S. Appl. No. 08/029,969, filed Mar. 13, 1990 (Equivalent of 0 387 527).

*Primary Examiner*—Manjunath N. Rao
*Assistant Examiner*—Christian L. Fronda
(74) *Attorney, Agent, or Firm*—Oblon, Spivak, McClelland, Maier & Neustadt, P.C.

(57) ABSTRACT

An isolated polynucleotide comprising a polynucleotide sequence selected from the group consisting of
a) polynucleotide which is at least 70% identical to a polynucleotide that codes for a polypeptide which comprises the amino acid sequence of SEQ ID. No. 2,
b) polynucleotide which codes for a polypeptide that comprises an amino acid sequence which is at least 70% identical to the amino acid sequence of SEQ ID No. 2,
c) polynucleotide which is complementary to the polynucleotides of a) or b), and p1 d) polynucleotide comprising at least 15 successive nucleotides of the polynucleotide sequence of a), b) or c), and processes for the fermentative preparation of L-amino acids using coryneform bacteria in which at least the metE gene is present in enhanced form, and the use of the polynucleotide sequences as hybridization probes.

35 Claims, 2 Drawing Sheets

Figure 1: Plasmid pCREmetAE
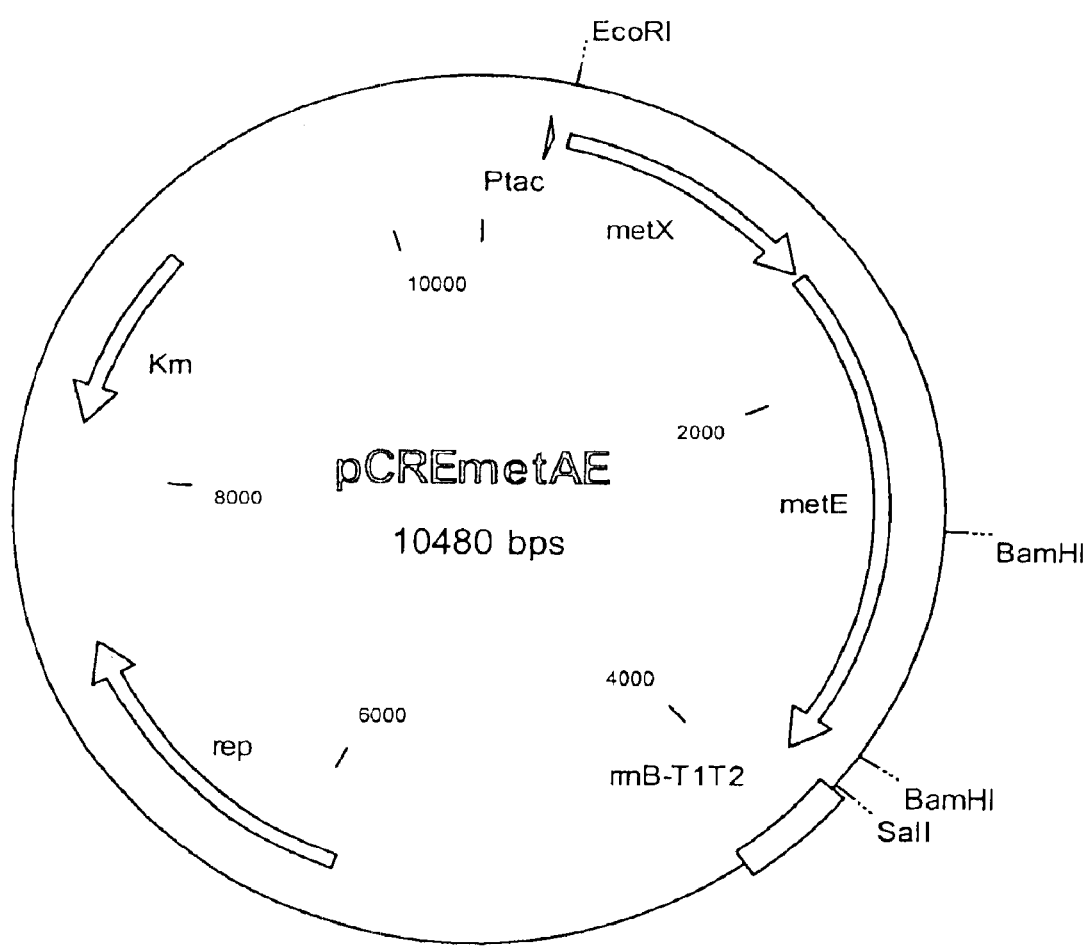

Figure 2: Plasmid pCREmetAEY
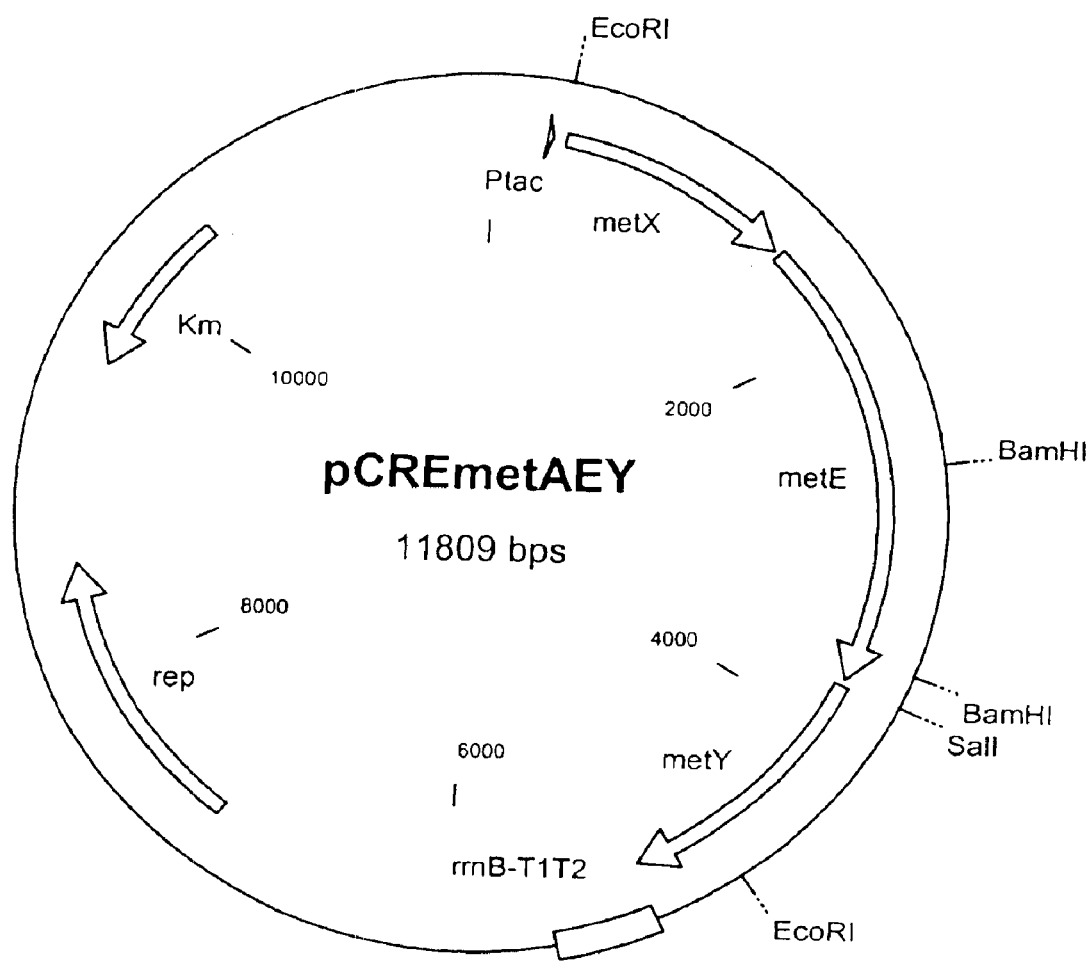

ISOLATED POLYNUCLEOTIDE FROM *CORYNEBACTERIUM* ENCODING A HOMOCYSTEINE METHYLTRANSFERASE

BACKGROUND OF THE INVENTION

1. Field of the Invention

The invention provides nucleotide sequences from coryneform bacteria which code for the metE gene and a process for the fermentative preparation of amino acids, in particular L-methionine, using bacteria in which the metE gene is enhanced.

2. Description of the Related Art

L-Amino acids, in particular L-methionine, are used in human medicine and in the pharmaceuticals industry, in the foodstuffs industry and very particularly in animal nutrition. It is known that amino acids are prepared by fermentation from strains of coryneform bacteria, in particular *Corynebacterium glutamicum*. Because of their great importance, work is constantly being undertaken to improve the preparation process. Improvements to the process can relate to fermentation measures stirring and supply of oxygen, or to the composition of the nutrient media such as the sugar concentration during the fermentation, or to the working up of the product by, for example, ion exchange chromatography, or to the intrinsic output properties of the microorganism itself.

Methods of mutagenesis, selection and mutant selection are used to improve the output properties of these microorganisms. Strains which are resistant to antimetabolites, such as e.g. the methionine analogue α-methyl-methionine, ethionine, norleucine, N-acetylnorleucine, S-trifluoromethylhomocysteine, 2-amino-5-heprenoitic acid, seleno-methionine, methionine-sulfoximine, methoxine, 1-aminocyclopentane-carboxylic acid, or are auxotrophic for metabolites of regulatory importance and produce amino acids, such as e.g. L-methionine, are obtained in this manner.

Recombinant DNA techniques have also been employed for some years for improving the *Corynebacterium* strains which produce L-amino acids, by amplifying individual amino acid biosynthesis genes and investigating their effect on the amino acid production.

SUMMARY OF THE INVENTION

An object of the present invention is to provide new measures for improved fermentative preparation of amino acids, in particular L-methionine.

When L-methionine or methionine are mentioned in the following, the salts, such as methionine hydrochloride or if methionine sulfate are also meant.

The invention provides an isolated polynucleotide from coryneform bacteria, comprising a polynucleotide sequence which codes for the metE gene, chosen from the group consisting of
a) polynucleotide which is at least 70% identical to a polynucleotide that codes for a polypeptide which comprises the amino acid sequence of SEQ ID No. 2,
b) polynucleotide which codes for a polypeptide that comprises an-amino acid sequence which is at least 70% identical to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), and the corresponding polypeptide having the enzymatic activity of homocysteine methyltransferase I.

The invention also provides the above-mentioned polynucleotides as DNA which is capable of replication, comprising:
(i) the nucleotide sequence shown in SEQ ID No. 1, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide comprising the nucleotide sequence as shown in SEQ ID No. 1;
a polynucleotide that codes for a polypeptide which comprises the amino acid sequence as shown in SEQ ID No. 2;
a vector containing the polynucleotide according to the invention, in particular a shuttle vector or plasmid vector, and
and coryneform bacteria serving as the host cell, which contain the vector or in which the metE gene is enhanced.

The invention also provides polynucleotides which are-obtained by screening a corresponding gene library, which comprises the complete gene having the polynucleotide sequence corresponding to SEQ ID No. 1, by means of hybridization with a probe which comprises the sequence of the polynucleotide mentioned, according to SEQ ID No. 1 or a fragment thereof, and isolation of the DNA sequence mentioned.

BRIEF DESCRIPTION OF THE FIGURES

FIG. 1 shows plasmid pCREmetAE.
FIG. 2 shows plasmid pCREmetAEY.

DETAILED DESCRIPTION OF THE PREFERRED EMBODIMENTS

Polynucleotides which comprise the sequences according to the invention are suitable as hybridization probes for RNA cDNA and DNA, in order to isolate, in the full length, nucleic acids or polynucleotides or genes which code for homocysteine methyltransferase I or to isolate those nucleic acids or polynucleotides or genes which have a high similarity of sequence or homology with that of the homocysteine methyltransferase I gene.

Polynucleotides according to the invention are furthermore suitable as primers with which the DNA of genes that code for homocysteine methyltransferase I can be prepared by the polymerase chain reaction (PCR).

Such oligonucleotides that serve as probes or primers comprise at least 30, preferably at least 20, very particularly at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds.

The polypeptides according to the invention include a polypeptide according to SEQ ID No. 2, in particular those with the biological activity of homocysteine methyltransferase I, and also those which are at least 70%, preferably at least 80% and in particular at least 90% to 95% identical to the polypeptide according to SEQ ID No. 2 and have the activity mentioned.

The invention moreover provides a process for the fermentative preparation of amino acids, in particular L-methionine, using coryneform bacteria which in particular already produce amino acids, and in which the nucleotide sequences which code for the metE gene are enhanced, in particular over-expressed.

The term "enhancements" in this connection describes an increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms which the present invention provides can prepare L-amino acids, in particular L-methionine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-methionine-producing strain

*Corynebacterium glutamicum* ATCC21608.

The new metE gene from *C. glutamicum* which codes for the enzyme homocysteine methyltransferase I (EC 2.1.1.14) has been isolated.

To isolate the metE gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction and recombination-defective. An example of these is the strain DH5αmcr, which has been described by Grant. et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the metE gene and which, as SEQ ID No. 1, is a constituent of the present invention has been found. The amino acid sequence of the corresponding protein has furthermore been derived from the present DNA sequence by the methods described above. The resulting amino-acid sequence of the metE gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. they are of neutral function.

It is furthermore known that changes at the N and/or C terminus of a protein must not substantially impair and may even stabilize the function thereof. Information in this context can be found in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found in the handbook by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids, in particular L-methionine, in an improved manner after over-expression of the metE gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-methionine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition-of the media and the culture procedure.

Instructions in this context can be found in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No 4,601,893, in Schwarzer and Puhler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application to WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the metE gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al., 1986, Gene 41: 337–342). The plasmid vector which contains the gene to be amplified is then transferred into the desired strain of *C. glutamicum* by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-methionine, to enhance one or more enzymes of the particular biosynthesis pathway, of glycolysis, of anaplerosis, of the citric acid cycle or of amino acid export, in addition to the metE gene.

Thus for the preparation of amino acids, in particular L-methionine, one or more genes chosen from the group consisting of the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the pyc gene which codes for pyruvate carboxylase (Eikmanns (1992), Journal of Bacteriology 174:6076–6086), the lysC gene which codes for a feed-back resistant aspartate kinase (Accession No. P26512; EP-B-0387527; EP-A-0699759), the metA gene which codes for homoserine O-acetyltransferase (ACCESSION Number AF052652), the metB gene which codes for cystathionine gamma-synthase (ACCESSION Number AF126953), the aecD gene which codes for cystathionine gamma-lyase (ACCESSION Number M89931)

the glyA gene which codes for serine hydroxymethyltransferase (JP-A-08107788), the metY gene which codes for O-acetylhomoserine sulfhydrylase (DSM 13556)

can be enhanced, in particular over-expressed.

It may furthermore be advantageous for the production of amino acids, in particular L-methionine, in addition to the enhancement of the metE gene, for one or more genes chosen from the group consisting of the thrB gene which codes for homoserine kinase (ACCESSION Number P08210), the ilvA gene which codes for threonine dehydratase (ACCESSION Number Q04513), the thrC gene which codes for threonine synthase (ACCESSION Number P23669), the ddh gene which codes for meso-diaminopimelate D-dehydrogenase (ACCESSION Number Y00151), the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7; DSM 13114)

to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

In addition to over-expression of the metE gene it may furthermore be advantageous for the production of amino acids, in particular L-methionine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of amino acids, in particular L-methionine. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic-nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Organic and inorganic sulfur-containing compounds, such as, for example, sulfides, sulfites, sulfates and thiosulfates, can be used as a source of sulfur, in particular for the preparation of methionine.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is furthermore also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements all or some of the biomass can be removed from the fermentation broth by separation methods, such as centrifugation, filtration, decanting or a combination thereof, or it can be left completely in. This broth is then thickened or concentrated by known methods, such as with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or-compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, Öle, Fette, Wachse 94, 12 (1968)).

As described here, "finely divided" means a powder with a predominant content (>50%) having a particle size of 20 to 200 μm diameter. "Coarse-grained" means products with a predominant content (>50%) having a particle size of 200 to 2000 μm diameter. In this context, "dust-free" means that the product contains only small contents (<5%) having particle sizes of less than 20 µm diameter. The particle size determination can be carried out with methods of laser diffraction spectrometry. The corresponding methods are described in the textbook on "Teilchengrößenmessung in der Laborpraxis" by R. H. Muller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, for example, silicas, silicates, grits, brans, meals, starches, sugars or others, and/or mixed and stabilized with conventional thickeners or binders. Use examples and processes in this context are described in the literature (Die Mühle+Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80%, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the group consisting of L-lysine, L-valine, L-threonine, L-alanine or L-tryptophan. They include vitamins chosen from the group consisting of vitamin B1 (thiamine), vitamin B2 (riboflavin), vitamin B5 (pantothenic acid), vitamin B6 (pyridoxine), vitamin B12 (cyanocobalamin), nicotinic acid/nicotinamide and vitamin E (tocopherol). They also include organic acids which carry one to three carboxyl groups, such as, acetic acid, lactic acid, citric acid, malic acid or fumaric acid. Finally, they also include sugars, such as, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention also provides a process for the preparation of an L-methionine-containing animal feedstuffs additive from fermentation broths, which comprises the steps a) culture and fermentation of an L-methionine-producing microorganism in a fermentation medium;

b) removal of water from the L-methionine-containing fermentation broth (concentration);

c) removal of an amount of 0 to 100 wt. % of the biomass formed during the fermentation; and d) drying of the fermentation broth obtained according to a) and/or b) to obtain the animal feedstuffs additive in the desired powder or granule form.

If desired, one or more of the following steps can furthermore be carried out in the process according to the invention:

e) addition of one or more organic substances, including L-methionine and/or D-methionine and/or the racemic mixture D,L-methionine, to the products obtained according to a), b) and/or c);

f) addition of auxiliary substances chosen from the group consisting of silicas, silicates, stearates, grits and bran to the substances obtained according to a) to d) for stabilization and to increase the storability; or g) conversion of the substances obtained according to a) to e) into a form stable to the animal stomach, in particular rumen, by coating with film-forming agents.

The analysis of L-methionine can be carried out by ion exchange chromatography with subsequent ninhydrin derivation, as described by Spackman et al. (Analytical Chemistry, 30, (1958), 1190).

The process according to the invention is used for the fermentative preparation of amino acids, in particular L-methionine.

The following microorganisms were deposited as a pure culture on 14th Jun. 2001 at the Deutsche Sammlung für Mikroorganismen und Zellkulturen (DSMZ=German Collection of Microorganisms and Cell Cultures, Braunschweig, Germany) in accordance with a the Budapest Treaty:

*Escherichia coli* DH5αmcr/pCREmetAE as DSM 14352,

*Escherichia coli* DH5αmcr/pCREmetAEY as DSM 14353.

The present invention is explained in more detail in the following with the aid of embodiment examples.

EXAMPLE 1

Preparation of a genomic cosmid gene library from *Corynebacterium glutamicum* ATCC 13032

Chromosomal DNA from *Corynebacterium glutamicum* ATCC-13032 was isolated as described by Tauch et al.

(1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2

Isolation and Sequencing of the metE Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αmcr (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/ Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 2235 base pairs, which was called the metE gene. The metE gene codes for a protein of 745 amino acids.

EXAMPLE 3

Preparation of the Strains *C. glutamicum* ATCC13032/ pCREmetA and ATCC13032/pCREmetAE 3.1 Amplification of the Genes metA and metE From the strain ATCC13032, chromosomal DNA was isolated by the method of Eikmanns et al. (Microbiology 140: 1817–1828 (1994)). Starting from the nucleotide sequences of the methionine biosynthesis genes metA (gene library Accession Number AF052652) and metE (SEQ ID No. 1) of *C. glutamicum* ATCC13032, the following oligonucleotides were chosen for the polymerase chain reaction (PCR) (see SEQ ID No. 3, SEQ ID No. 4, SEQ ID No. 5 and SEQ ID No. 6):

metA-EVP5:
5'-AGAACGAATTCAAAGGAGGACAACCATGCCC ACCCTCGCGC-3'
metA-EVP3:
5'-GTCGTGGATCCCCTATTAGATGTAGAACTCG-3'
metE-EVP5:
5'-GGCTCAAAAGATCTAAAGGAGGACAACCA TGACTTCCAACTTTTCTTC-3'
metE-EVP3:
5'-GGTTCCT GTCGACGGTACCATTTAGATAGTTGCTCCGATT-3'

The primers shown were synthesized by MWG-Biotech AG (Ebersberg, Germany) and the PCR reaction was carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 1161 bp in size, which carries the metA gene, and a DNA fragment 2286 bp in size, which carries the metE gene.

Furthermore, the primer metA-EVP5 contains the sequence for the sleavage site of the restriction endonuclease EcoRI, the primer metA-EVP3 the cleavage site of the restriction endonuclease BamHI, the primer metE-EVP5 the cleavage site of the restriction endonuclease BglII and the primer metE-EVP3 the cleavage site of the restriction endonuclease SalI, which are marked by underlining in the nucleotide sequence shown above.

The metA fragment 1161 bp in size was cleaved with the restriction endonucleases EcoRI and BamHI, and the metE fragment 2286 bp in size was cleaved with the restriction endonucleases BglII and SalI. The two batches were separated by gel electrophoresis and the fragments metA (approx. 1150 bp) and metE (approx. 2270 bp) were then isolated from the agarose gel with the QiaExII Gel Extraction Kit (Product No. 20021, Qiagen, Hilden, Germany).

3.2 Cloning of metA in the Vector pZ8-1

The *E. coli-C. glutamicum* shuttle expression vector pZ8-1 (EP 0 375 889) was used as the base vector for the expression.

DNA of the plasmid pZ8-1 was cleaved completely with the restriction enzymes EcoRI and BamHI and then dephosphorylated with shrimp alkaline phosphatase (Roche Diagnostics GmbH, Mannheim, Germany, Product Description SAP, Product No. 1758250).

The metA fragment approx. 1150 bp in size isolated from the agarose gel in example 3.1 and cleaved with the restriction endonucleases BamHI and EcoRI was mixed with the vector pZ8-1 prepared in this way and the batch was treated with T4 DNA ligase (Amersham Pharmacia, Freiburg, Germany, Product Description T4-DNA-Ligase, Code no. 27-0870-04).

The ligation batch was transformed in the *E. coli* strain DH5αmcr (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinat individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetA.

3.3 Cloning of metE in the Vector pCREmetA

The plasmid pCREmetA described in example 3.2 was cleaved completely with the restriction enzymes BamHI and SalI and then dephosphorylated with shrimp alkaline phosphatase (Roche Diagnostics GmbH, Mannheim, Germany, Product Description SAP, Product No. 1758250).

The metE fragment approx. 2270 bp in size obtained in example 3.1 by means of the polymerase chain reaction and cleaved with the restriction endonucleases BglII and SalI was mixed with the vector pCREmetA prepared in this way. The batch was treated with T4 DNA ligase (Amersham Pharmacia, Freiburg, Germany, Product Description T4-DNA-Ligase, Code no. 27-0870-04).

The ligation batch was transformed in the *E. coli* strain DH5αmcr (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant-with the Qiaprep Spin Miniprep Kit (Product No. 27106, Qiagen, Hilden, Germany) in accordance with the manufacturer's instructions and checked by restriction cleavage. The resulting plasmid was called pCREmetAE. It is shown in FIG. 1. The strain *E. coli* DH5αmcr/pCREmetAE was deposited as a pure culture on 14th Jun. 2001 at the Deutsche Sammlung für Mikroorganismen und Zellkulturen (DSMZ=German Collection of Microorganisms and Cell Cultures, Braunschweig, Germany) in accordance with the Budapest Treaty as DSM 14352.

3.4 Preparation of the Strains *C. glutamicum* ATCC23032/pCREmetA and ATCC13032/pCREmetAE The vectors pCREmetA and pCREmetAE obtained in example 3.2 and 3.3 were electroporated in the strain *C. glutamicum* ATCC*13032* using the electroporation method described by Liebl et al. (FEMS Microbiology Letters, 53:299–303 (1989)). Selection of the plasmid-carrying cells took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l is kanamycin. Incubation was carried out for 2 days at 33° C.

Plasmid DNA was isolated from in each case one transformant by conventional methods (Peters-Wendisch et al., 1998, Microbiology 144, 915–927) and checked by restriction cleavage. The resulting strains were called ATCC13032/pCREmetA and ATCC13032/pCREmetAE.

EXAMPLE 4

Preparation of L-methionine with the Strain *C. glutamicum* ATCC13032/pCREmetAE

The *C. glutamicum* strains ATCC13032/pCREmetA and ATCC13032/pCREmetAE obtained in example 3 were cultured in a nutrient medium suitable for the production of methionine and the methionine content in the culture supernatant was determined.

For this, the strains were first incubated on an agar plate with the corresponding antibiotic (brain-heart agar with kanamycin (50 mg/l)) for 24 hours at 33° C. Starting from this agar plate culture, in each case a preculture was seeded (10 ml medium in a 100 ml conical flask). The complete medium CgIII was used as the medium for the precultures.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Kanamycin (25 mg/l) was added to this. The preculture was incubated for 16 hours at 33° C. at 240 rpm on a shaking machine. In each case a main culture was seeded from these precultures such that the initial OD (660 nm) of the main cultures was 0.1. Medium MM was used for the main cultures.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |

-continued

| Medium MM | |
|---|---|
| MnSO₄ * H₂O | 5.0 mg/l |
| Biotin (sterile-filtered) | 0.3 mg/l |
| Thiamine * HCl (sterile-filtered) | 0.2 mg/l |
| CaCO₃ | 25 g/l |

The CSL, MOPS and the salt solution were brought to pH 7 with aqueous ammonia and autoclaved. The sterile substrate and vitamin solutions were then added, as well as the CaCO₃ autoclaved in the dry state.

Culturing is carried out in a 10 ml volume in 100 ml conical flasks with baffles. Kanamycin (25 mg/l) was added. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of methionine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Methionine mg/l |
|---|---|---|
| ATCC13032/pCREmetA | 12.3 | 6.6 |
| ATCC13032/pCREmetAE | 14.3 | 15.3 |

EXAMPLE 5

Preparation of the strain *C. glutamicum* ATCC13032/pCREmetAEY 5.1 Amplification of the metY Gene From the strain ATCC13032, chromosomal DNA was isolated by the method of Eikmanns et al. (Microbiology 140: 1817–1828 (1994)). Starting from the nucleotide sequence of the methionine biosynthesis gene metY (DE: 10043334.0) of *C. glutamicum* ATCC13032, the following oligonucleotides were chosen for the polymerase chain reaction (PCR) (see SEQ ID No. 7 and SEQ ID No. 8):

metY-EVP5:
5'-CTAATAAGTCGACAAAGGAGGACAACCATGCC AAAGTACGAC-3'
metY-EVP3:
5'-GAGTCTA ATGCATGCTAGATTGCAGCAAAGCCG-3'

The primers shown were synthesized by MWG-Biotech AG (Ebersberg, Germany) and the PCR reaction was carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 1341 bp in size, which carries the metY gene.

Furthermore, the primer metY-EVP5 contains the sequence for the cleavage site of the restriction endonuclease SalI and the primer metY-EVP3 the cleavage site of the restriction endonuclease NsiI, which are marked by underlining in the nucleotide sequence shown above.

The metY fragment 1341 bp in size was cleaved with the restriction endonucleases SalI and NsiI. The batch was separated by gel electrophoresis and the fragment metY (approx. 1330 bp) was then isolated from the agarose gel with the QiaExII Gel Extraction Kit (Product No. 20021, Qiagen, Hilden, Germany).

5.2 Cloning of metA and metY in the Vector pZ8-1

The plasmid pCREmetA described in example 3.2 was cleaved completely with the restriction enzymes SalI and PstI and then dephosphorylated with shrimp alkaline phosphatase (Roche Diagnostics GmbH, Mannheim, Germany, Product Description SAP, Product No. 1758250).

The metY fragment approx. 1330 bp in size isolated from the agarose gel in example 5.1 and cleaved with the restriction endonucleases SalI and NsiI was mixed with the vector pCREmetA prepared in this way and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5αmcr (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetAY.

5.3 Cloning of metE in the Vector pCREmetAY

The plasmid pCREmetAY described in example 5.2 was cleaved completely with the restriction enzymes BamHI and SalI and then dephosphorylated with shrimp alkaline phosphatase (Roche Diagnostics GmbH, Mannheim, Germany, Product Description SAP, Product No. 1758250).

The metE fragment approx. 2270 bp in size obtained in example 3.1 by means of the polymerase chain reaction and cleaved with the resriction endonucleases BglII and SalI was mixed with the vector pCREmetAY prepared in this way. The batch was treated with T4 DNA ligase (Amersham Pharmacia, Freiburg, Germany, Product Description T4-DNA-Ligase, Code no. 27-0870-04).

The ligation batch was transformed in the *E. coli* strain DH5αmcr (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:90) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetAEY. It is shown in FIG. 2. The strain *E. coli* DH5αmcr/pCREmetAEY was deposited as a pure culture on 14th Jun. 2001 at the Deutsche Sammlung für Mikroorganismen und Zellkulturen (DSMZ=German Collection of Microorganisms and Cell Cultures, Braunschweig, Germany) in accordance with the Budapest Treaty as DSM 14353.

5.4 Preparation of the Strain *C. glutamicum* ATCC13032/pCREmetAEY

The vector pCREmetAY obtained in example 5.3 was electroporated in the strain *C. glutamicum* ATCC13032 using the electroporation method described by Liebl et al. (FEMS Microbiology Letters, 53:299–303 (1989)). Selection of plasmid-carrying cells took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology 144, 915–927) and checked by restriction cleavage. The resulting strain was called ATCC13032pCREmetAEY.

EXAMPLE 6

Fermentative Preparation of L-methionine with the strain ATCC13032/pCREmetAEY

The strain C. glutamicum ATCC13032/pCREmetAEY constructed by the process described in example 4 was cultured in a nutrient medium' suitable for the production of methionine and the methionine content in the culture supernatant was determined.

For this, the strain was first incubated on an agar plate with the corresponding antibiotic (brain-heart agar with kanamycin (25 mg/i)) for 24 hours at 33° C. Starting from this agar plate culture, a preculture was seeded (10 ml medium in a 100 ml conical flask). The medium MM-1 was used as the medium for the preculture.

| Medium MM-1 | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.01 mg/l |
| Vitamin B12 (sterile-filtered) | 0.02 mg/l |
| Thiamine * HCl (sterile-filtered) | 0.2 mg/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state. Kanamycin (25 mg/l) was added to this.

The preculture was incubated for 16 hours at 33° C. at 240 rpm on a shaking machine and then used as the inoculum for the main culture in the fermenter. To establish an optical density (at 660 nm) of 1.0 as the starting value for the main culture in the fermenter, the corresponding amount of culture broth was transferred from the preculture.

The medium MM-2, which has the following composition, was used for the main culture:

| Medium MM-2 | |
|---|---|
| CSL (corn steep liquor) | 5 g/l |
| Glucose (autoclaved separately) | 50 g/l |
| Salts: | |
| $(NH_4)_2SO_4$ | 25 g/l |
| $KH_2PO_4$ | 0.1 g/l |

| -continued | |
|---|---|
| Medium MM-2 | |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.01 mg/l |
| Vitamin B12 (sterile-filtered) | 0.02 mg/l |
| Thiamine * HCl (sterile-filtered) | 0.2 mg/l |
| Antifoam (Structol) | 0.5 g/l |

All the components of the medium were initially introduced directly into the fermenter, dissolved in water and then sterilized by means of heat (121° C., 20 minutes). Only the glucose was prepared in a stock solution of 50 wt. % and sterilized separately (also 121° C., 20 minutes). Biotin or thiamine were sterile-filtered and added under aseptic conditions directly before the start of fermentation.

Culturing was carried out by the batch process in a bioreactor with a working volume of 0.5 L (Multifermenter SIXFORS from Infors GmbH, Bodmingen, Switzerland). After addition of the inoculum, the starting volume in the fermenter was 0.4 L in total. Further culturing was carried out under constant aeration (0.1 vvm ("volume per volume per minute") and stirring at 33° C. and a pH of 7.0. Correction or adjustment of the pH was carried out with a 5% $NH_4OH$ solution. The set value for the concentration of dissolved oxygen in the fermentation medium was regulated at 40% and adjusted via the stirrer speed at a constant rate of aeration.

After 48 hours the process was ended and the optical density (OD) of the culture suspension was determined with an LP2W photometer from Dr. Lange (Berlin, Germany) at a measurement wavelength of 660 nm. The concentration of L-methionine formed was determined with an amino acid analyzer from Eppendorf-BioTronik (Hamburg, Germany) by ion exchange chromatography and post-column derivation with ninhydrin detection.

An optical density in the final sample of 31.7 and a concentration of L-methionine of 39.0 mg per liter could be determined by the methods described above as the result.

EXAMPLE 7

Preparation of Biomass-Free Broth Containing L-methionine

The biomass was first separated off from a fermentation broth comprising L-methionine prepared by the process of example 6 and comprising about 39 mg/l L-methionine. For this, 0.5 l of the above-mentioned fermentation broth was centrifuged with a laboratory centrifuge of the Biofuge-Stratos type from Heraeus (Düsseldorf, Germany) for 20 minutes at 4,000 rpm and the supernatant from the centrifugation was then purified further by cross-flow ultrafiltration with an MRC polymer membrane of 30 kD in an ultrafiltrations unit from ICT GmbH (Bad Homburg, Germany).

EXAMPLE 8

Preparation of a Biomass-Free Product Comprising L-methionine to from a Fermentation Broth The biomass was first separated off from a fermentation broth comprising L-methionine prepared by the process as described under example 6 and comprising about 39.0 mg/l L-methionine. For this, the fermenter contents of the above-mentioned fermentation broth were centrifuged and subjected to ultrafiltration as described in example 7.

23.7 g pure L-methionine (>99%; MERCK, Darmstadt, Germany) were then added batchwise to 300 g of the biomass-free filtrate, while stirring, in order to establish the desired content of L-methionine in the product. The suspension comprising L-methionine treated in this way was then mixed with 150 g water, with further stirring, to improve the working-up properties.

A portion of the suspension improved in this way was then lyophilized in a freeze-dryer of the type LYOVAC GT 2 from Leybold (Cologne, Germany). The product comprising L-methionine prepared in this manner had a content of 70 wt. % L-methionine and was free flowing.

The remaining portion of the suspension improved in this way was treated by means of spray drying in a laboratory spray dryer of the Büchi-190 type from Büchi-Labortechnik GmbH (Constance, Germany) at an intake temperature of 170° C., a starting temperature of 105° C., a pressure difference of −40 mbar and an air flow rate of 600 NL/h. The product comprising L-methionine prepared in this manner had a content of 70 wt. % L-methionine and was free-flowing.

EXAMPLE 9

Preparation of a Biomass-Containing Product Comprising L-methionine from a Fermentation Broth From a fermentation broth comprising L-methionine prepared by the process of example 6 and comprising about 39 mg/l L-methionine, 23.7 g pure L-methionine (>99%; MERCK, Darmstadt, Germany) was first added batchwise, while stirring, in order to establish the desired content of L-methionine in the product. The fermentation broth treated in this way was then mixed with 150 g water, with further stirring, to improve the working-up properties.

A portion of this biomass-containing broth was then lyophilized in a freeze-dryer of the type LYOVAC GT 2 from Leybold (Cologne, Germany). The product comprising L-methionine prepared in this way had a content of 65 wt. % L-methionine and was free-flowing.

The remaining portion of the biomass-containing broth was treated by means of spray drying in a laboratory spray dryer of the Büchi-190 type from Büchi-Labortechnik GmbH (Constance, Germany) at an intake temperature of 170° C., a starting temperature of 105° C., a pressure difference of −40 mbar and an air flow rate of 600 NL/h. The product comprising L-methionine prepared in this way had a content of 65 wt. % L-methionine and was free-flowing.

BRIEF DESCRIPTION OF THE FIGURES

FIG. 1: Plasmid pCREmetAE

FIG. 2: pCREmetAEY

The abbreviations used in the figures have the following meaning:

Km: Resistance gene for kanamycin
metE: metE gene of *C. glutamicum*
metY: metY gene of *C. glutamicum*
metA: metA gene of *C. glutamicum*
Ptac: tac promoter
rrnB-T1T2: Terminator T1T2 of the rrnB gene of *E. coli*
rep: Plasmid-coded replication origin for *C. glutamicum* (of pHM1519)
BamHI: Cleavage site of the restriction enzyme BamHI
EcoRI: Cleavage site of the restriction enzyme EcoRI
SalI; Cleavage site of the restriction enzyme SalI This disclosure is based on priority documents DE 100 38 023.9, DE 101 09 689.5 and U.S. 60/294,250, each incorporated by reference.

Obviously, numerous modifications of the invention are possible in view of the above teachings. Therefore, within the scope of the appended claims; the invention may be practiced otherwise than as specifically described herein.

What is claimed is:

1. An isolated polynucleotide which encodes a polypeptide comprising the amino acid sequence of SEQ ID NO: 2 or a fragment of SEQ ID NO: 2 having homocysteine methyltransferase I activity.

2. The isolated polynucleotide of claim 1, which comprises SEQ ID NO: 1.

3. The isolated polynucleotide of claim 1, which consists of the polynucleotide of SEQ ID NO: 1.

4. The isolated polynucleotide of claim 1, which encodes a polypeptide consisting of a fragment SEQ ID NO: 2 having homocysteine methyltransferase I activity.

5. The isolated polynucleotide of claim 1, which encodes a polypeptide comprising the amino acid sequence of SEQ ID NO: 2.

6. The isolated polynucleotide of claim 1, which is RNA.

7. A vector of comprising the isolated polynucleotide of claim 1.

8. The vector of claim 7, further comprising one or more promoter(s), regulation region(s), ribosome binding site(s), or expression cassette(s).

9. The vector of claim 7, which is capable of replication in a coryneform bacterium.

10. A host cell transformed with the isolated polynucleotide of claim 1.

11. The host cell of claim 10 comprising more than one copy of said isolated polynucleotide.

12. The host cell of claim 10, wherein said isolated polynucleotide is present on a plasmid.

13. The host cell of claim 10, wherein said isolated polynucleotide is integrated in the chromosome.

14. The host cell of claim 10, which is a coryneform bacterium.

15. The host cell of claim 10, which is *Corynebacterium glutamicum*.

16. *Escherichia coli* strain DHαmcr/pCREmetAE deposited as DSM 14352 at the Deutsche Sammlung für Mikroorganismen und Zellkulturen (German Collection of Microorganisms and Cell Cultures), Braunschweig, Germany.

17. *Escherichia coli* strain DHαmcr/pCREmetAEY deposited as DSM 14353 at the Deutsche Sammlung für Mikroorganismen und Zellkulturen (German Collection of Microorganisms and Cell Cultures), Braunschweig, Germany.

18. An isolated polynucleotide which is the full complement of the isolated polynucleotide of claim 1.

19. A process for the preparation of L-methionine, comprising:

a) growing a coryneform bacterium in which the polynucleotide of claim 1 is over-expressed in a medium suitable for the production of said L-methionine, and b) recovering, and optionally purifying said L-methionine.

20. The process of claim 19, wherein over-expression is achieved by increasing the copy number of said polynucleotide.

21. The process of claim 19, wherein said coryneform bacterium is transformed with a plasmid vector which carries the polynucleotide sequence of claim 1.

22. The process of claim 21, wherein the coryneform bacterium contains multiple copies of said plasmid.

23. The process of claim 19, wherein the coryneform bacterium has one or more over-expressed polypeptide(s) encoded by at least one polynucleotide selected from the group consisting of:

the lysC polynucleotide which codes for a feed back resistant aspartate kinase, the gap polynucleotide which codes for glyceraldehyde 3-phosphate dehydrogenase, the pgk polynucleotide which codes for 3-phosphoglycerate kinase, the pyc polynucleotide which codes for pyruvate carboxylase, the tpi polynucleotide which codes for triose phosphate isomerase, the meta polynucleotide which codes for homoserine O-acetyltransferase, the metB polynucleotide which codes for cystathionine gamma-synthase, the aecD polynucleotide which codes for cystathionine gamma-lyase, the glyA polynucleotide which codes for serine hydroxymethyltransferase, and the metY polynucleotide which codes for O-acetylhomoserine sulfhydrylase.

24. The process of claim 19, wherein the coryneform bacterium has reduced expression of one or more polypeptide(s) encoded by at least one polynucleotide selected from the group comprising of:

the thrB polynucleotide which codes for homoserine kinase, the ilvA polynucleotide which codes for threonine dehydratase, the thrC polynucleotide which codes for threonine synthase, the ddh polynucleotide which codes for meso-diaminopimelate D-dehydrogenase, the pck polynucleotide which codes for phosphoenol pyruvate carboxykinase, the pgi polynucleotide which codes for glucose 6-phosphate isomerase, and the poxB polynucleotide which codes for pyruvate oxidase.

25. The process of claim 19, wherein a said coryneform bacterium is *Corynebacterium glutamicum*.

26. The process of claim 25, wherein said *Corynebacterium glutamicum* is strain ATCC13032/pCREmetAE.

27. The process of claim 25, wherein said *Corynebacterium glutamicum* is strain ATCC13032/pCREmetAEY.

28. A process for the preparation of an L-methionine-containing animal feedstuffs additive comprising:

a) culturing an L-methionine-producing microorganism in which the polynucleotide sequence of claim 1 has been over-expressed in a fermentation medium for a time and under conditions suitable for production of L-methionine;

b) removing water from the L-methionine-containing fermentation broth (concentration); and/or c) removing an amount of 0 to 100 wt. % of the biomass formed during fermentation; and, optionally, d) drying the fermentation broth obtained according to b) and/or c) to obtain the animal feedstuffs additive in a powder or granule form.

29. The process of claim 28, wherein multiple copies of the polynucleotide of claim 1 are expressed in said microorganism.

30. The process of claim 28, wherein said L-methionine-producing microorganism is *Corynebacterium glutamicum*.

31. The process of claim 30, wherein said *Corynebacterium glutamicum* is strain ATCC13032/pCREmetAE.

32. The process of claim 30, wherein said *Corynebacterium glutamicum* is strain ATCC13032/pCREmetAEY.

33. The process of claim 28, further comprising one or more of the following steps:

e) adding L-methionine and/or D-methionine and/or the racemic mixture D,L-methionine, to the products obtained according to b), c) and/or d);

f) adding at least one conventional carrier substances selected from the group consisting of silicas, silicates, stearates, grits and bran to the products obtained according to b) to e); and/or g) converting the substances obtained according to b) to f) into a form stable in rumen, by coating them with a film-forming agent.

34. The process of claim 28, wherein a portion of the biomass is removed in c).

35. The process of claim 34, wherein about 100% of the biomass is removed in c).

* * * * *

SEQUENCE LISTING

```
<160> NUMBER OF SEQ ID NOS: 8

<210> SEQ ID NO 1
<211> LENGTH: 2810
<212> TYPE: DNA
<213> ORGANISM: Corynebacterium glutamicum
<220> FEATURE:
<221> NAME/KEY: CDS
<222> LOCATION: (317)..(2551)
<223> OTHER INFORMATION:

<400> SEQUENCE: 1
agcccaaaac ggcaccatga atttaaatcc ccggaacttc ttgacagacc gagcagtcta      60
gggtttggtt gaaaacgcaa tcggttcact tttaatcctc tccctggagc cccggatgat     120
gaggaacgcc aaagctttct gaatggaaat tttaagcgtt aagtgggacg acctcgatta     180 caaaaggcg aggaaacccc cggggcagct ttctgccacc cggtgatttc gcgaaccttg     240
aaacatcgtc agaagattgc cgtgcgtcct agccgggatc cgcacgttcg gctcaagcag     300 aaagtctttta actcac atg act tcc aac ttt tct tcc act gtc gct ggt ctt    352
                    Met Thr Ser Asn Phe Ser Ser Thr Val Ala Gly Leu
                     1               5                  10 cct cgc atc gga gcg aag cgt gaa ctg aag ttc gcg ctc gaa ggc tac        400
Pro Arg Ile Gly Ala Lys Arg Glu Leu Lys Phe Ala Leu Glu Gly Tyr
```

```
                15                  20                  25
tgg aat gga tca att gaa ggt cgc gaa ctt gcg cag acc gcc cgc caa      448
Trp Asn Gly Ser Ile Glu Gly Arg Glu Leu Ala Gln Thr Ala Arg Gln
         30                  35                  40 ttg gtc aac act gca tcg gat tct ttg tct gga ttg gat tcc gtt ccg      496
Leu Val Asn Thr Ala Ser Asp Ser Leu Ser Gly Leu Asp Ser Val Pro
 45                  50                  55                  60 ttt gca gga cgt tcc tac tac gac gca atg ctc gat acc gcc gct att      544
Phe Ala Gly Arg Ser Tyr Tyr Asp Ala Met Leu Asp Thr Ala Ala Ile
                 65                  70                  75 ttg ggt gtg ctg ccg gag cgt ttt gat gac atc gct gat cat gaa aac      592
Leu Gly Val Leu Pro Glu Arg Phe Asp Asp Ile Ala Asp His Glu Asn
             80                  85                  90 gat ggt ctc cca ctg tgg att gac cgc tac ttt ggc gct gct cgc ggt      640
Asp Gly Leu Pro Leu Trp Ile Asp Arg Tyr Phe Gly Ala Ala Arg Gly
         95                  100                 105 act gag acc ctg cct gca cag gca atg acc aag tgg ttt gat acc aac      688
Thr Glu Thr Leu Pro Ala Gln Ala Met Thr Lys Trp Phe Asp Thr Asn
 110                 115                 120 tac cac tac ctc gtg ccg gag ttg tct gcg gat aca cgt ttc gtt ttg      736
Tyr His Tyr Leu Val Pro Glu Leu Ser Ala Asp Thr Arg Phe Val Leu
 125                 130                 135                 140 gat gcg tcc gcg ctg att gag gat ctc cgt tgc cag cag gtt cgt ggc      784
Asp Ala Ser Ala Leu Ile Glu Asp Leu Arg Cys Gln Gln Val Arg Gly
                 145                 150                 155 gtt aat gcc cgc cct gtt ctg gtt ggt cca ctg act ttc ctt tcc ctt      832
Val Asn Ala Arg Pro Val Leu Val Gly Pro Leu Thr Phe Leu Ser Leu
             160                 165                 170 gct cgc acc act gat ggt tcc aat cct ttg gat cac ctg cct gca ctg      880
Ala Arg Thr Thr Asp Gly Ser Asn Pro Leu Asp His Leu Pro Ala Leu
         175                 180                 185 ttt gag gtc tac gag cgc ctc atc aag tct ttc gat act gag tgg gtt      928
Phe Glu Val Tyr Glu Arg Leu Ile Lys Ser Phe Asp Thr Glu Trp Val
 190                 195                 200 cag atc gat gag cct gcg ttg gtc acc gat gtt gct cct gag gtt ttg      976
Gln Ile Asp Glu Pro Ala Leu Val Thr Asp Val Ala Pro Glu Val Leu
 205                 210                 215                 220 gag cag gtc cgc gct ggt tac acc act ttg gct aag cgc gat ggc gtg     1024
Glu Gln Val Arg Ala Gly Tyr Thr Thr Leu Ala Lys Arg Asp Gly Val
                 225                 230                 235 ttt gtc aat act tac ttc ggc tct ggc gat cag gcg ctg aac act ctt     1072
Phe Val Asn Thr Tyr Phe Gly Ser Gly Asp Gln Ala Leu Asn Thr Leu
             240                 245                 250 gcg ggc atc ggc ctt ggc gcg att ggc gtt gac ttg gtc acc cat ggc     1120
Ala Gly Ile Gly Leu Gly Ala Ile Gly Val Asp Leu Val Thr His Gly
         255                 260                 265 gtc act gag ctt gct gcg tgg aag ggt gag gag ctg ctg gtt gcg ggc     1168
Val Thr Glu Leu Ala Ala Trp Lys Gly Glu Glu Leu Leu Val Ala Gly
 270                 275                 280 atc gtt gat ggt cgt aac att tgg cgc acc gac ctg tgt gct gct ctt     1216
Ile Val Asp Gly Arg Asn Ile Trp Arg Thr Asp Leu Cys Ala Ala Leu
 285                 290                 295                 300 gct tcc ctg aag cgc ctg gca gct cgc ggc cca atc gca gtg tct acc     1264
Ala Ser Leu Lys Arg Leu Ala Ala Arg Gly Pro Ile Ala Val Ser Thr
                 305                 310                 315 tct tgt tca ctg ctg cac gtt cct tac acc ctc gag gct gag aac att     1312
Ser Cys Ser Leu Leu His Val Pro Tyr Thr Leu Glu Ala Glu Asn Ile
             320                 325                 330 gag cct gag gtc cgc gac tgg ctt gcc ttc ggc tcg gag aag atc acc     1360
```

-continued

| | | |
|---|---|---|
| Glu Pro Glu Val Arg Asp Trp Leu Ala Phe Gly Ser Glu Lys Ile Thr<br>335 340 345 | | |
| gag gtc aag ctg ctt gcc gac gcc cta gcc ggc aac atc gac gcg gct<br>Glu Val Lys Leu Leu Ala Asp Ala Leu Ala Gly Asn Ile Asp Ala Ala<br>350 355 360 | | 1408 |
| gcg ttc gat gcg gcg tcc gca gca att gct tct cga cgc acc tcc cca<br>Ala Phe Asp Ala Ala Ser Ala Ala Ile Ala Ser Arg Arg Thr Ser Pro<br>365 370 375 380 | | 1456 |
| cgc acc gca cca atc acg cag gaa ctc cct ggc cgt agc cgt gga tcc<br>Arg Thr Ala Pro Ile Thr Gln Glu Leu Pro Gly Arg Ser Arg Gly Ser<br>385 390 395 | | 1504 |
| ttc gac act cgt gtt acg ctg cag gag aag tca ctg gag ctt cca gct<br>Phe Asp Thr Arg Val Thr Leu Gln Glu Lys Ser Leu Glu Leu Pro Ala<br>400 405 410 | | 1552 |
| ctg cca acc acc acc att ggt tct ttc cca cag acc cca tcc att cgt<br>Leu Pro Thr Thr Thr Ile Gly Ser Phe Pro Gln Thr Pro Ser Ile Arg<br>415 420 425 | | 1600 |
| tct gct cgc gct cgt ctg cgc aag gaa tcc atc act ttg gag cag tac<br>Ser Ala Arg Ala Arg Leu Arg Lys Glu Ser Ile Thr Leu Glu Gln Tyr<br>430 435 440 | | 1648 |
| gaa gag gca atg cgc gaa gaa atc gat ctg gtc atc gcc aag cag gaa<br>Glu Glu Ala Met Arg Glu Glu Ile Asp Leu Val Ile Ala Lys Gln Glu<br>445 450 455 460 | | 1696 |
| gaa ctt ggt ctt gat gtg ttg gtt cac ggt gag cca gag cgc aac gac<br>Glu Leu Gly Leu Asp Val Leu Val His Gly Glu Pro Glu Arg Asn Asp<br>465 470 475 | | 1744 |
| atg gtt cag tac ttc tct gaa ctt ctc gac ggt ttc ctc tca acc gcc<br>Met Val Gln Tyr Phe Ser Glu Leu Leu Asp Gly Phe Leu Ser Thr Ala<br>480 485 490 | | 1792 |
| aac ggc tgg gtc caa agc tac ggc tcc cgc tgt gtt cgt cct cca gtg<br>Asn Gly Trp Val Gln Ser Tyr Gly Ser Arg Cys Val Arg Pro Pro Val<br>495 500 505 | | 1840 |
| ttg ttc gga aac gtt tcc cgc cca gcg cca atg act gtc aag tgg ttc<br>Leu Phe Gly Asn Val Ser Arg Pro Ala Pro Met Thr Val Lys Trp Phe<br>510 515 520 | | 1888 |
| cag tac gca cag agc ctg acc cag aag cat gtc aag gga atg ctc acc<br>Gln Tyr Ala Gln Ser Leu Thr Gln Lys His Val Lys Gly Met Leu Thr<br>525 530 535 540 | | 1936 |
| ggt cca gtc acc atc ctt gca tgg tcc ttc gtt cgc gat gat cag ccg<br>Gly Pro Val Thr Ile Leu Ala Trp Ser Phe Val Arg Asp Asp Gln Pro<br>545 550 555 | | 1984 |
| ctg gct acc act gct gac cag gtt gca ctg gca ctg cgc gat gaa att<br>Leu Ala Thr Thr Ala Asp Gln Val Ala Leu Ala Leu Arg Asp Glu Ile<br>560 565 570 | | 2032 |
| aac gat ctc atc gag gct ggc gcg aag atc atc cag gtg gat gag cct<br>Asn Asp Leu Ile Glu Ala Gly Ala Lys Ile Ile Gln Val Asp Glu Pro<br>575 580 585 | | 2080 |
| gcg att cgt gaa ctg ttg ccg cta cga gac gtc gat aag cct gcc tac<br>Ala Ile Arg Glu Leu Leu Pro Leu Arg Asp Val Asp Lys Pro Ala Tyr<br>590 595 600 | | 2128 |
| ctg cag tgg tcc gtg gac tcc ttc cgc ctg gcg act gcc ggc gca ccc<br>Leu Gln Trp Ser Val Asp Ser Phe Arg Leu Ala Thr Ala Gly Ala Pro<br>605 610 615 620 | | 2176 |
| gac gac gtc caa atc cac acc cac atg tgc tac tcc gag ttc aac gaa<br>Asp Asp Val Gln Ile His Thr His Met Cys Tyr Ser Glu Phe Asn Glu<br>625 630 635 | | 2224 |
| gtg atc tcc tcg gtc atc gcg ttg gat gcc gat gtc acc acc atc gaa<br>Val Ile Ser Ser Val Ile Ala Leu Asp Ala Asp Val Thr Thr Ile Glu<br>640 645 650 | | 2272 |

-continued

```
gca gca cgt tcc gac atg cag gtc ctc gct gct ctg aaa tct tcc ggc    2320
Ala Ala Arg Ser Asp Met Gln Val Leu Ala Ala Leu Lys Ser Ser Gly
            655                 660                 665 ttc gag ctc ggc gtc gga cct ggt gtg tgg gat atc cac tcc ccg cgc    2368
Phe Glu Leu Gly Val Gly Pro Gly Val Trp Asp Ile His Ser Pro Arg
        670                 675                 680 gtt cct tcc gcg cag gaa gtg gac ggt ctc ctc gag gct gca ctg cag    2416
Val Pro Ser Ala Gln Glu Val Asp Gly Leu Leu Glu Ala Ala Leu Gln
685                 690                 695                 700 tcc gtg gat cct cgc cag ctg tgg gtc aac cca gac tgt ggt ctg aag    2464
Ser Val Asp Pro Arg Gln Leu Trp Val Asn Pro Asp Cys Gly Leu Lys
                705                 710                 715 acc cgt gga tgg cca gaa gtg gaa gct tcc cta aag gtt ctc gtt gag    2512
Thr Arg Gly Trp Pro Glu Val Glu Ala Ser Leu Lys Val Leu Val Glu
            720                 725                 730 tcc gct aag cag gct cgt gag aaa atc gga gca act atc taaattgggt    2561
Ser Ala Lys Gln Ala Arg Glu Lys Ile Gly Ala Thr Ile
        735                 740                 745 taccgctagg aacccaaaga ttaagggcac gagtgtcacc aggattgccg cacccatggc    2621
aacaccgaag gacaccgtgc ccactcctat ttgcatcaca cgcccaagg tagcggcgcc    2681 caaaacagcg cccacctggc gtgaggtgtt gtaaaaacca gaagcagagc ccactaaatc    2741
ctgcggaaca tcacgcagag caatcacaga gttcggtgca aaactcatcg cgttggagct    2801
accgaacaa                                                            2810

<210> SEQ ID NO 2
<211> LENGTH: 745
<212> TYPE: PRT
<213> ORGANISM: Corynebacterium glutamicum

<400> SEQUENCE: 2

Met Thr Ser Asn Phe Ser Ser Thr Val Ala Gly Leu Pro Arg Ile Gly
1               5                   10                  15

Ala Lys Arg Glu Leu Lys Phe Ala Leu Glu Gly Tyr Trp Asn Gly Ser
            20                  25                  30

Ile Glu Gly Arg Glu Leu Ala Gln Thr Ala Arg Gln Leu Val Asn Thr
        35                  40                  45

Ala Ser Asp Ser Leu Ser Gly Leu Asp Ser Val Pro Phe Ala Gly Arg
    50                  55                  60

Ser Tyr Tyr Asp Ala Met Leu Asp Thr Ala Ala Ile Leu Gly Val Leu
65                  70                  75                  80

Pro Glu Arg Phe Asp Asp Ile Ala Asp His Glu Asn Asp Gly Leu Pro
                85                  90                  95

Leu Trp Ile Asp Arg Tyr Phe Gly Ala Ala Arg Gly Thr Glu Thr Leu
            100                 105                 110

Pro Ala Gln Ala Met Thr Lys Trp Phe Asp Thr Asn Tyr His Tyr Leu
        115                 120                 125

Val Pro Glu Leu Ser Ala Asp Thr Arg Phe Val Leu Asp Ala Ser Ala
    130                 135                 140

Leu Ile Glu Asp Leu Arg Cys Gln Gln Val Arg Gly Val Asn Ala Arg
145                 150                 155                 160

Pro Val Leu Val Gly Pro Leu Thr Phe Leu Ser Leu Ala Arg Thr Thr
                165                 170                 175

Asp Gly Ser Asn Pro Leu Asp His Leu Pro Ala Leu Phe Glu Val Tyr
            180                 185                 190

Glu Arg Leu Ile Lys Ser Phe Asp Thr Glu Trp Val Gln Ile Asp Glu
```

-continued

```
                195                 200                 205
Pro Ala Leu Val Thr Asp Val Ala Pro Glu Val Leu Glu Gln Val Arg
    210                 215                 220
Ala Gly Tyr Thr Thr Leu Ala Lys Arg Asp Gly Val Phe Val Asn Thr
225                 230                 235                 240
Tyr Phe Gly Ser Gly Asp Gln Ala Leu Asn Thr Leu Ala Gly Ile Gly
            245                 250                 255
Leu Gly Ala Ile Gly Val Asp Leu Val Thr His Gly Val Thr Glu Leu
                260                 265                 270
Ala Ala Trp Lys Gly Glu Leu Leu Ala Gly Ile Val Asp Gly
    275                 280                 285
Arg Asn Ile Trp Arg Thr Asp Leu Cys Ala Ala Leu Ala Ser Leu Lys
    290                 295                 300
Arg Leu Ala Ala Arg Gly Pro Ile Ala Val Ser Thr Ser Cys Ser Leu
305                 310                 315                 320
Leu His Val Pro Tyr Thr Leu Glu Ala Glu Asn Ile Glu Pro Glu Val
                325                 330                 335
Arg Asp Trp Leu Ala Phe Gly Ser Glu Lys Ile Thr Glu Val Lys Leu
                340                 345                 350
Leu Ala Asp Ala Leu Ala Gly Asn Ile Asp Ala Ala Phe Asp Ala
                355                 360                 365
Ala Ser Ala Ala Ile Ala Ser Arg Arg Thr Ser Pro Arg Thr Ala Pro
    370                 375                 380
Ile Thr Gln Glu Leu Pro Gly Arg Ser Arg Gly Ser Phe Asp Thr Arg
385                 390                 395                 400
Val Thr Leu Gln Glu Lys Ser Leu Glu Leu Pro Ala Leu Pro Thr Thr
                405                 410                 415
Thr Ile Gly Ser Phe Pro Gln Thr Pro Ser Ile Arg Ser Ala Arg Ala
                420                 425                 430
Arg Leu Arg Lys Glu Ser Ile Thr Leu Glu Gln Tyr Glu Glu Ala Met
    435                 440                 445
Arg Glu Glu Ile Asp Leu Val Ile Ala Lys Gln Glu Glu Leu Gly Leu
    450                 455                 460
Asp Val Leu Val His Gly Glu Pro Glu Arg Asn Asp Met Val Gln Tyr
465                 470                 475                 480
Phe Ser Glu Leu Leu Asp Gly Phe Leu Ser Thr Ala Asn Gly Trp Val
                485                 490                 495
Gln Ser Tyr Gly Ser Arg Cys Val Arg Pro Pro Val Leu Phe Gly Asn
            500                 505                 510
Val Ser Arg Pro Ala Pro Met Thr Val Lys Trp Phe Gln Tyr Ala Gln
            515                 520                 525
Ser Leu Thr Gln Lys His Val Lys Gly Met Leu Thr Gly Pro Val Thr
530                 535                 540
Ile Leu Ala Trp Ser Phe Val Arg Asp Asp Gln Pro Leu Ala Thr Thr
545                 550                 555                 560
Ala Asp Gln Val Ala Leu Ala Leu Arg Asp Glu Ile Asn Asp Leu Ile
                565                 570                 575
Glu Ala Gly Ala Lys Ile Ile Gln Val Asp Glu Pro Ala Ile Arg Glu
            580                 585                 590
Leu Leu Pro Leu Arg Asp Val Asp Lys Pro Ala Tyr Leu Gln Trp Ser
        595                 600                 605
Val Asp Ser Phe Arg Leu Ala Thr Ala Gly Ala Pro Asp Asp Val Gln
610                 615                 620
```

```
Ile His Thr His Met Cys Tyr Ser Glu Phe Asn Glu Val Ile Ser Ser
625                 630                 635                 640

Val Ile Ala Leu Asp Ala Asp Val Thr Thr Ile Glu Ala Ala Arg Ser
            645                 650                 655

Asp Met Gln Val Leu Ala Ala Leu Lys Ser Ser Gly Phe Glu Leu Gly
        660                 665                 670

Val Gly Pro Gly Val Trp Asp Ile His Ser Pro Arg Val Pro Ser Ala
    675                 680                 685

Gln Glu Val Asp Gly Leu Leu Glu Ala Ala Leu Gln Ser Val Asp Pro
690                 695                 700

Arg Gln Leu Trp Val Asn Pro Asp Cys Gly Leu Lys Thr Arg Gly Trp
705                 710                 715                 720

Pro Glu Val Glu Ala Ser Leu Lys Val Leu Val Glu Ser Ala Lys Gln
                725                 730                 735

Ala Arg Glu Lys Ile Gly Ala Thr Ile
            740                 745

<210> SEQ ID NO 3
<211> LENGTH: 41
<212> TYPE: DNA
<213> ORGANISM: Artificial sequence
<220> FEATURE:
<223> OTHER INFORMATION: Synthetic DNA

<400> SEQUENCE: 3
agaacgaatt caaaggagga caaccatgcc caccctcgcg c                    41

<210> SEQ ID NO 4
<211> LENGTH: 31
<212> TYPE: DNA
<213> ORGANISM: Artificial sequence
<220> FEATURE:
<223> OTHER INFORMATION: Synthetic DNA

<400> SEQUENCE: 4
gtcgtggatc ccctattaga tgtagaactc g                               31

<210> SEQ ID NO 5
<211> LENGTH: 47
<212> TYPE: DNA
<213> ORGANISM: Artificial sequence
<220> FEATURE:
<223> OTHER INFORMATION: Synthetic DNA

<400> SEQUENCE: 5
ggctcaaaga tctaaggag gacaaccatg acttccaact tttcttc               47

<210> SEQ ID NO 6
<211> LENGTH: 40
<212> TYPE: DNA
<213> ORGANISM: Artificial sequence
<220> FEATURE:
<223> OTHER INFORMATION: Synthetic DNA

<400> SEQUENCE: 6
ggttcctgtc gacggtacca tttagatagt tgctccgatt                      40

<210> SEQ ID NO 7
<211> LENGTH: 42
<212> TYPE: DNA
<213> ORGANISM: Artificial sequence
<220> FEATURE:
```

-continued

```
<223> OTHER INFORMATION: Synthetic DNA

<400> SEQUENCE: 7
ctaataagtc gacaaaggag gacaaccatg ccaaagtacg ac          42

<210> SEQ ID NO 8
<211> LENGTH: 33
<212> TYPE: DNA
<213> ORGANISM: Artificial sequence
<220> FEATURE:
<223> OTHER INFORMATION: Synthetic DNA

<400> SEQUENCE: 8
gagtctaatg catgctagat tgcagcaaag ccg                    33
```